United States Patent [19]

von Behrens

[11] Patent Number: 4,710,021
[45] Date of Patent: Dec. 1, 1987

[54] PARTICULATE MATTER ANALYZING APPARATUS AND METHOD

[75] Inventor: Wieland E. von Behrens, Chicago, Ill.
[73] Assignee: Sequoia-Turner Corporation, Mountain View, Calif.
[21] Appl. No.: 837,875
[22] Filed: Mar. 5, 1986

Related U.S. Application Data

[63] Continuation of Ser. No. 542,224, Oct. 14, 1983, abandoned.
[51] Int. Cl.$^4$ ..................... G01N 15/12; G01N 15/14; G01N 21/85
[52] U.S. Cl. .................... 356/72; 324/71.4; 356/73; 377/11; 377/12
[58] Field of Search .................... 356/72, 73; 324/71.4; 377/10—12

[56] References Cited

U.S. PATENT DOCUMENTS

| | | | |
|---|---|---|---|
| 2,656,508 | 10/1953 | Coulter | 324/71 |
| 2,869,078 | 1/1959 | Coulter et al. | 324/71 |
| 3,299,354 | 1/1967 | Hogg | 324/71 CP |
| 3,444,464 | 5/1969 | Coulter et al. | 324/71 |
| 3,739,258 | 6/1973 | Karuhn et al. | 324/71 CP |
| 3,739,268 | 6/1973 | Karuhn et al. | 324/71 CP |
| 3,746,976 | 7/1973 | Hogg | 324/71 CP |
| 3,810,010 | 5/1974 | Thom | 324/71 CP |
| 3,871,770 | 3/1975 | von Behrens et al. | 356/103 |
| 3,902,115 | 8/1975 | Hogg et al. | 324/71 CP |
| 3,979,669 | 9/1976 | Godin | 324/71 CP |
| 4,165,484 | 8/1979 | Haynes | 324/71 CP |
| 4,198,160 | 4/1980 | Kachel et al. | 356/72 |
| 4,253,058 | 2/1981 | Kachel et al. | 324/71.1 |
| 4,361,803 | 11/1982 | Hogg | 324/71.4 |

OTHER PUBLICATIONS

"Hydrodynamic Focusing and Electronic Cell-Sizing Techniques," by M. L. Shuler, R. Aris & H. M. Tsuchiya, Applied Microbiology, 9/72.
"Development & Application of a Rapid Cell Sorter," by H. R. Hulett, W. Bonner, R. Sweet & L. Herzenberg; Clin. Chem., vol. 19, #8; 1973.
"Comparison of Techniques Improving Resolution of Standard Coulter Cell Sizing Systems," by von Behrens et al., Jrnl. of Hist. etc. 1976.
"Electrical Sizing and Counting of Platelets in Whole Blood," by J. Schulz & R. Thom; Medical & Biological Engineering; Jul. 1973.
"Means for Orienting Flat Cells in Flow Systems," by Stovel et al., Biophysics Journal, vol. 23, No. 1; 1978.
"Enhanced Light Collection in a Flow Cytometer," by M. H. Fox et al., Cytometry, vol. 1, No. 1.
"A New Multiparameter Separator for Microscopic Particles and Biological Cells," by Steinkamp et al. Rev. Sci. Instrum., vol. 44, #9, 9/73.
"Methodik und Ergebnisse optischer Formfaktoruntersuchungen bei der Zellvolumenmessung nach Coulter," Microscopica Acta; 1974.
"Studies on the Coulter Counter, Part 1, . . . " by Karuhm et al., Powder Technoloy, 11(1975)157–171 (printed in the Netherlands).
"Studies on the Coulter Counter, Part II . . . " R. Davies et al., Powder Technology, 00(1975)00–00 (printed in the Netherlands).
Sheet entitled "Clay Adams ULTRA-FLO 100 Whole Blood Platelet Counter," (vB73 Transducer).

Primary Examiner—Vincent P. McGraw
Attorney, Agent, or Firm—Flehr, Hohbach, Test, Albritton & Herbert

[57] ABSTRACT

A method and apparatus for jetting a measured volume of a suspension of particulates such as blood cells or colloids into a single fluid-primed incompletely partitioned transducer chamber in such a way that the dynamic relationship between the priming liquid and the inflowing jet imparts to the suspended particulates the properties of a stable stream line monofile which reliably traverses one or more particulate-identifying and/or analyzing sensing zones. Said transducer chamber has one or more of the following three sources of energy for moving the contained fluids: an easily maintained non-critical pressure differential between the suspension inflow port and an exit line, potential energy stored within the transducer chamber during the priming step, a pump mechanism to propel particulate-free fluid. The measurement period in all such transducers may be defined by monitoring the volume of either the inflowing or displaced outflowing liquid.

13 Claims, 15 Drawing Figures

PARTICULATE MATTER ANALYZING APPARATUS AND METHOD

This is a continuation of application Ser. No. 542,224 filed Oct. 14, 1983, now abandoned.

This invention relates generally to particulate matter analyzing methods and apparatus and more particularly to apparatus for reliably counting and analyzing particulate matter suspended in a liquid medium and caused to flow in a fully-controlled manner through various sensing or measuring zones.

There are many types of particulate counting and analyzing apparatus presently available. A large subgroup of these is represented by methodologies for evaluating particulates suspended in a flowing fluid medium in such a way that the systems basically generate analyzable signals from one suspended element at a time. Both methodologically and historically these systems can be grouped into four broad categories: the simple exact counters giving very reliable counts in narrowly defined fields of application, which do not require that each signal from a particulate or element be very precisely interpretable in terms of the physical characteristics or chemical composition of the element; the pure analyzers giving superb resolution of the physical characteristics and/or chemical composition of the suspended particulates or elements but not having convenient counting capabilities; low-cost hybrid systems which compromise the performance of the potential counting and analyzing capabilities but do perform certain non-critical screening tasks; and, expensive high resolution analytical counters which preserve the important exact and convenient counting capability of the pure counters at great cost.

The universally known Coulter counters of the 1950s and 1960s which exploited the elegant metering U.S. Pat. No. 2,869,078 are a paradigm for the pure counters. Technically the particle count of a suspension is the number density which is rigorously defined as the precisely determined number of the elements in every unit of volume of the representative suspension. In the pure exact counters, the great reliability and precision in the generated counts is achieved by direct application of the Archimedes-Pascal principle, that if a solid or fluid is introduced into a closed vessel full of such fluid, then unless enormous forces are used, an exactly equivalent volume of fluid must be displaced from the vessel (and can therefore be used instead of an inserted solid plunger to meter the inflowing volume) and must also traverse any defined section across laminar flow lines between the inflow and outflow ports. If one or more constrictions occur between the input and output planes (such as a particle sensor of the Coulter type described in U.S. Pat. No. 2,656,508 or one of the many other sensors described in U.S. Pat. No. 3,871,770), then exactly the same volume of fluid which flows in at the inflow and out at the outflow must flow through each sensor.

Unfortunately, the range over which these types of elegant counters can be used with analytical sensitivity is greatly limited by the fact that, no matter how small we make a sensing constriction (such as the Coulter sensing orifice) both the hydrodynamic and the energy field within the sensing region will always be non-uniform in relation to characteristics of interest of the suspended elements. For example, the electric field of a Coulter sensing orifice extends far out to either side of the actual cylindrical hole in the dividing wall which separates the two electrodes. Hence, large particulates on the downstream or waste side of the orifice can enter or, in the case of recently arrived particles which have traversed the orifice, re-enter the sensing zone and cause signals of such a character and magnitude that they prevent the meaningful counting or analysis of small particles traversing the sensing zone along stable stream lines originating on the inflow side. Additionally, such uncontrolled circulation of particles routinely causes deposits and precipitations in the critical sensing zone regions, such as microscope lenses or laser ports or electrical-sensing orifices and frequently vitiates the counting function of the pure simple counters.

Many prior art patents purport to ameliorate the field inhomogeneity deficiencies of existing analyzic counters. U.S. Pat. No. 3,902,115 addresses this issue. However, like all other effective known methods for reliably overcoming this very general problem, the effect of the complex solution offered in the patent is to give up the theoretically essential characteristic of an exact counter—the direct metering of the volume which contains the enumerated particles. In U.S. Pat. No. 3,902,115 the suspension of particles is caused to flow through the sensing region on the basis of a pressure differential maintained between the inflow and outflow ports but, in addition, a stream of particle free diluent is introduced into the transducer vessel and into the critical region of the sensing zone to maintain the electrical fringe field of the sensor clear of previously analyzed particulates. This effectively introduces a variable amount of fluid into the metering system. This results in significant uncertainty in the particulate concentration.

The principles realized in the pure analyzers which do not offer exact counting capability are taught in sufficient detail in my U.S. Pat. No. 3,871,770. The theoretical requirements for achieving high particle size resolution for automated counting of particulates of the order of size of mammalian blood cells involve bringing the particulates into a very precisely defined geometric and temporal relationship to any one of various sensing zones.

The described apparatus is only one of the many types of apparatus which provide a sufficiently controlled relationship between the particulates in the sensing zones and the critical energy fields of the sensing zones. Coulter U.S. Pat. No. 3,902,115 also teaches a suitable apparatus. However, all the many types of structure which achieve the high analytical resolution through better control of the particulate trajectory through the sensing regions of the transducers represent open systems in the sense that the transducer chamber is no longer a fluid filled vessel having only one inflow and one outflow port for accurately measuring volume during a well-defined counting period. For example, certain vessels have an air-fluid or gas-fluid interface, most vessels introduce one or more streams of particulate-free fluid during the counting period, and most of the apparatus is merely termed an analyzer or a sizer without any claims relating to the capability of convenient exact counting. In my patent the major emphasis was on sizing and on multiparametric analysis without any detailed reference to the fundamental problem of exact counting.

The relatively low-cost hybrid counting particulate analyzers represent compromise systems which perform a number of arduous analytical and counting tasks as well as they might be performed by more laborious (and therefore impractical) manual methodologies. However, they generally compromise or violate both the principle of direct meassurement of the volume of the analyzed suspension and the principle of maintaining sufficient control over the trajectory of the particulates through the one or several sensing zones in the system.

Prior to the invention described herein, adequate counting ability in a flow analyzer was only achieved at the cost of extreme complexity. Such complexity is very expensive, and with every additional non-fluidic component, there has been a corresponding increase in the probability of malfunction.

The present invention provides an improved method and apparatus for generating stable fully-controlled stream lines of suspended particulates in such a way that they predictably traverse one or more critical sensing regions within a partially subdivided closed vessel. A closed vessel is defined as one in which the volume of introduced suspension can be measured exactly by the displacement or movement of fluid at either the inflow or the outflow end of the defined structure. The invention teaches a method for making precisely this same volume of fluid traverse any given plane placed across a fully controlled trajectory of the inflowing suspension within the chamber, this exact equivalence being maintained throughout the counting period of the apparatus. This provides both high resolution analytic capability and high precision counting capability separately as well as in combination. The constant unidirectional fluid movement is achieved by shooting a jet of the suspension into the compound fluid-primed transducer chamber from a fine capillary or orifice at the inflow end of the chamber; allowing this jet to pass coherently through the contained particle free fluid to some distal portion of the chamber in which waste or analyzed suspension can accumulate safely for the duration of the counting cycle; permitting the pressure represented by this accumulating fluid to displace its own volume of particle free fluid; and straddling the created stable stream lines with various sensors for interrogating, analyzing and counting the suspended particulate matter. Furthermore, the initially contained particle free fluid from a portion of that distal chamber is used to satisfy the venturi needs of the jet stream in its transit through the chamber.

In the simplest embodiments of this invention, we realize two principles: the principle that no moving mechanical transducer parts apart from the movement of particulate free and particulate containing fluid are required within the compound transducer chamber, and the principle that the readily created and maintained pressure differential between definable inflow and outflow (or upstream and downstream) ends of the structure is utilized as the primary energy source for creating the desired flows within the transducer chamber. However, whereas in my U.S. Pat. No. 3,871,770 and in similar devices the pressure differential is maintained merely across an upstream and a downstream end of one or more sensing regions, in the present invention that pressure differential is maintained between the inflow and outflow regions of a single vessel, through said vessel is partidally subdivided and may be compound and multiphasic. The vessle, however, must be single and continuous in the sense that Pascal's principle for stationary fluid is observed: namely, that when the pressure at any point on that enclosed resting fluid is changed, then the pressure changes by an equal amount at all points in the fluid. Any partial subdivision within the chamber and any sensors arranged in or about the chamber will not affect this property of the invention.

In addition, the present invention exploits the fact, unrecognized by previous patents in this field, that particulates passing through an orifice, continue to travel in a straight line unless acted on by a force. By exploiting this fact along with Bernoulli's Principle within the closed fluid-filled compound chamber, we can tolerate movement of the particle free fluid in diverse manners and directions within the compound chamber so long as the net total fluid movement across readily defined inflow and outflow planes of the overall single chamber is identical to the total net movement of the suspension across the critical planes of any of the one or more analytic sensors.

In more sophisticated embodiments of this invention in which one achieves relatively long stable particulate monofiles, one may supplement the kinetic motive force for the movement of particle free fluid (i.e., that force which is created within the closed chamber by exploiting the kinetic energy of the rapidly moving inflowing jet) with potential energy which is previously stored within the single closed but compound chamber. One may even supply electromagnetic or comparable energy from without to propel the particle free fluid within the closed chamber as with a pump.

In certain of these more elaborate embodiments of the invention, there may also be energy transparent or energy opaque mobile walls made of fluids, semi-solids, or solids within the overall closed chamber.

It is therefore an object of the present invention to provide an improved analyzing apparatus for analyzing suspended particulate matter.

It is another object of the present apparatus which forms a jet stream which travels through a particulate free region where it can be sensed and analyzed and in which fluid displacement at its inflow or outflow is a measure of the volume traversing each sensor.

It is another object of the present invention to provide a particulate matter analyzing apparatus in which the particulate matter flows through an orifice or aperture to form a jet stream with entrained particles which travels to a region which captures the particles and prevents them from interfering with measurements made at the orifice.

It is a further object of the invention to provide a particle counting and/or analyzing apparatus which is effective and simple in construction.

It is another object of the present invention to provide a particle analyzing apparatus in which the particles flow through a measuring orifice or aperture and are jetted into a region which captures the particles and prevents them from interfering with measurements at the orifice.

The foregoing and other objects of the invention may be more clearly understood from the following description taken in conjunction with the accompanying drawing of which.

Figure 1:
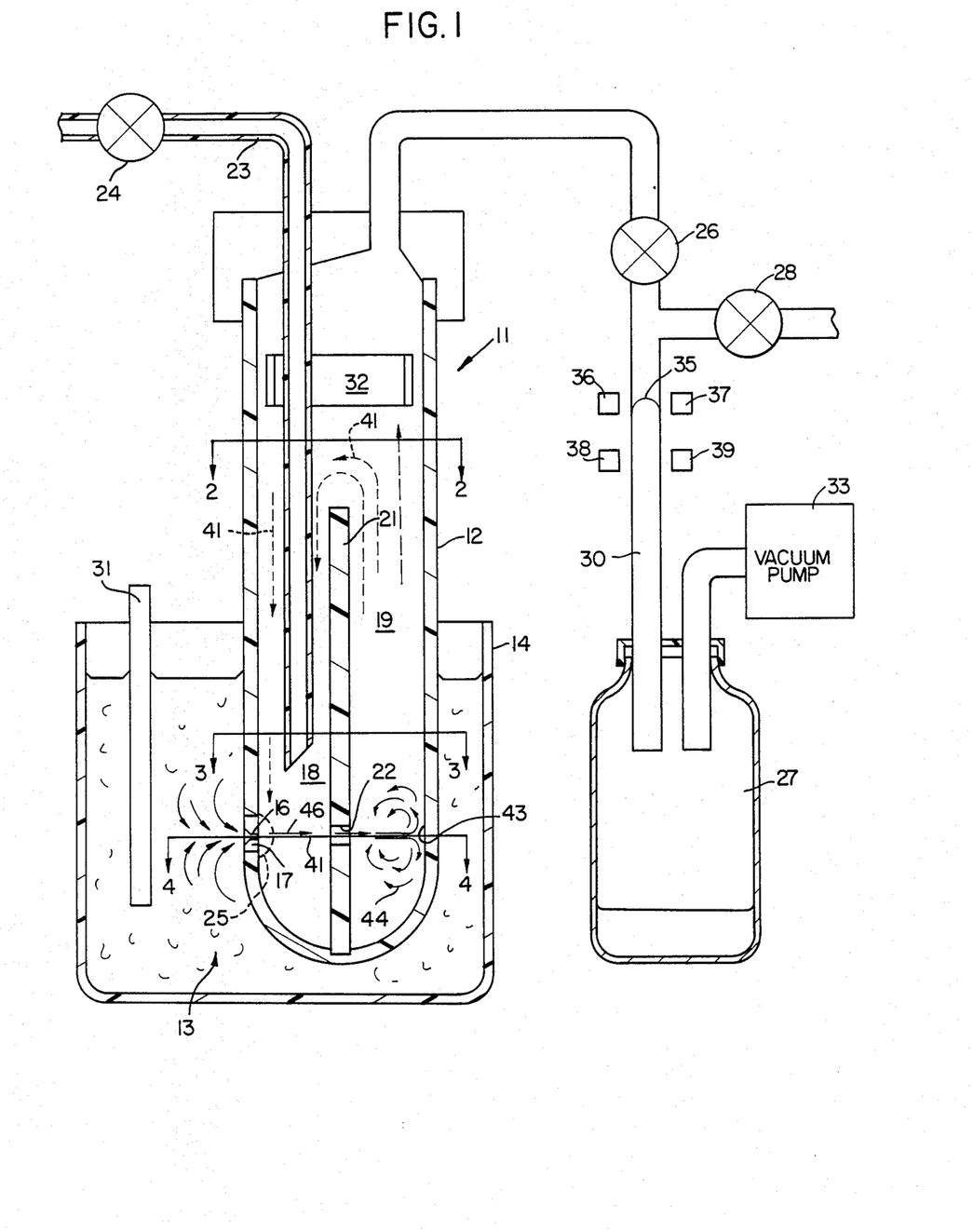
FIG. 1 is a sectional view of the particle counting and analyzing apparatus in accordance with one embodiment of the invention including a schematic diagram of an associated flow control.
Figure 2:
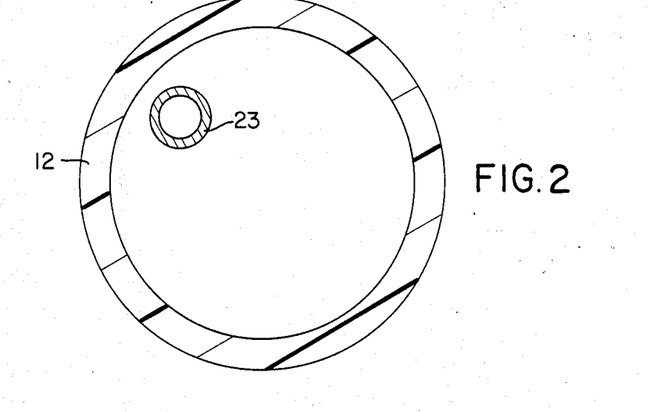
FIG. 2 is a sectional view taken along the line 2—2 of FIG. 1.
Figure 3:
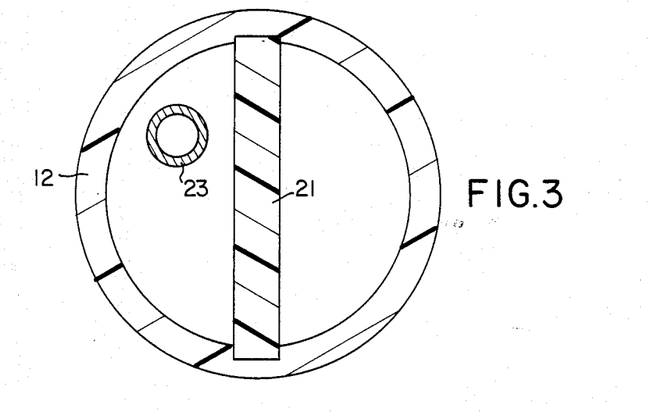
FIG. 3 is a sectional view taken along the line 3—3 of FIG. 1.
Figure 4:
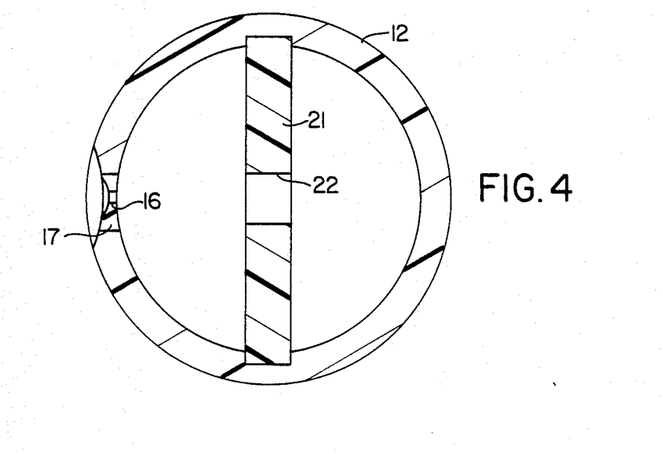
FIG. 4 is a sectional view taken along the line 4—4 of FIG. 1.
Figure 5:
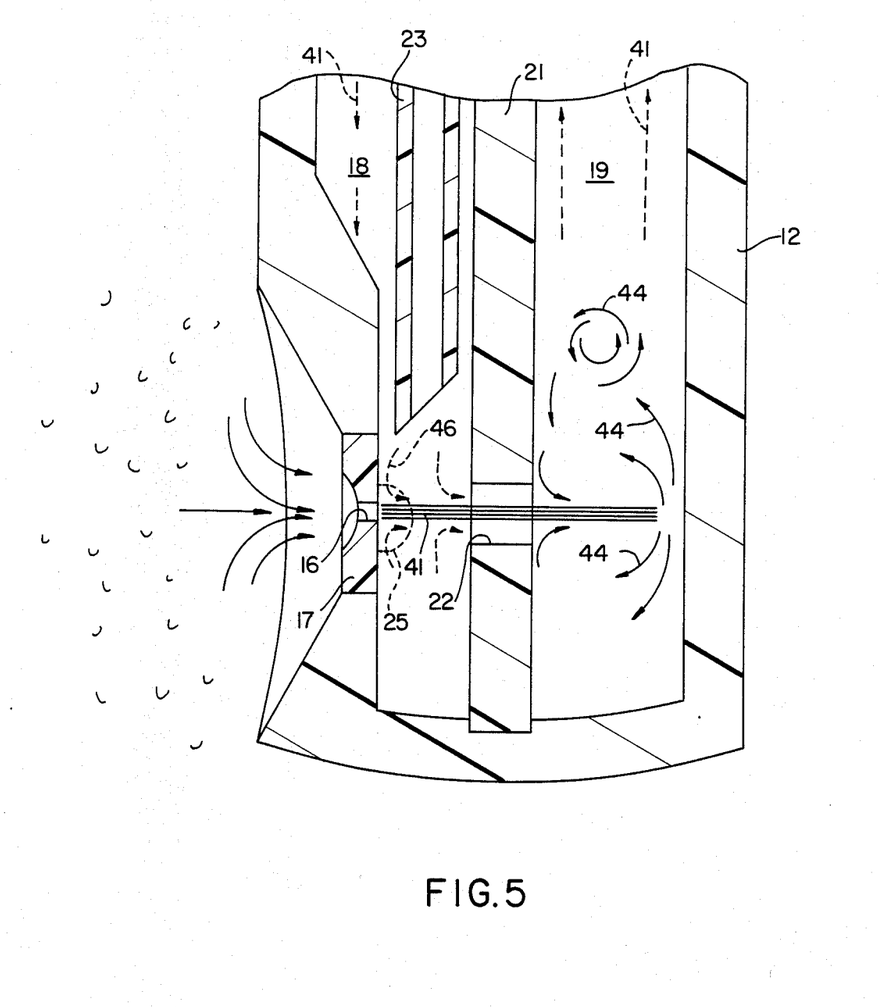
FIG. 5 is an enlarged view of the particle analyzing apparatus of FIG. 1 showing the jet stream and particulate matter and particle free liquid flow paths.

In common with prior art apparatus, the embodiment shown in FIG. 1 counts and analyzes suspended particulate matter by causing the liquid and entrained particulate matter to pass through a measuring orifice or aperture through which also passes an electric current. The particulate matter changes the conductance through the aperture and modulates the electric current. Particles are counted and sized by processing the current. Generally the particle containing solution is disposed on one side of an aperture and a clean electrolyte on the other side. A pressure differential causes the particle bearing solution to pass through the aperture. A predetermined directly metered volume of solution is passed through the aperture and particles counted to give a measure of concentration. The electrical current waveform is analyzed to give indication of size, shape and composition of the particles.

FIGS. 1–5 show one embodiment of the present invention. The particle analyzing apparatus 11 includes an apertured tube 12 immersed in solution 13 which contains the particulate matter in suspension. The solution is disposed in container 14. The tube 12 includes an analyzing aperture or orifice 16 communicating between the interior and exterior of the tube. The aperture 16 may be formed in jewel 17 which is suitably secured to the body of the tube 12. The tube 12 is subdivided into two regions 18 and 19 by a dividing wall 21. The wall 21 includes an isolation aperture 22 disposed opposite, in line with, and spaced from, the aperture 16. The tube 12 is initially filled with particle free liquid via the fill tube 23. The filling is controlled by the valve 24. The tube is filled by opening outlet valve 26 and filling under suction until liquid flows past valve 26. Valves 24 and 26 are then closed. The valve 28 is opened to allow the total portion of the drain tube 30 to empty. The valve 28 is then closed. The complete volume between the valves 24 and 26 is then filled with liquid.

Current is caused to flow through the orifice 16 by applying a voltage between electrode 31 in the solution 13 and the electrode 32 in the particle free liquid. The valve 26 is then opened and vacuum is applied to the drain 27 via vacuum pump 33. The liquid front at valve 26 then advances toward the drain 27 as sample is drawn through the aperture 16. When the liquid front 35 reaches a first light-photocell 36, 37, the apparatus begins to count particles flowing through orifice 16 by counting appropriate voltage fluctuations. When the liquid front 35 reaches the second light-photocell 38, 39, the counting is stopped. Other means such as conductive electrodes may be employed to sense the position of the liquid front. This provides the number of particles in the given volume represented by the body of fluid between photo-cells 37 and 39. After one or more runs the apparatus is refilled with clean electrolyte by opening valves 24 and 26. By using a closed volume the measure of the outflow volume is an exact measure of the inflow volume through the analyzing orifice.

The improvement provided by the present invention is that the particulate laden fluid is prevented from recirculating adjacent the orifice 16 and the ability to provide an exact volume measure. By applying a vacuum to the entire body of fluid in the tube 12 a pressure drop is created directly across the orifice. This causes particulate laden solution to jet through the orifice in a defined focused stream line 41 which jets through the internal electric fringe field 25 of the measuring orifice and through the opening 22 after which it strikes the wall 43 and recirculates. However, the recirculating particles are kept away from the rear of the orifice 16 and therefore do not alter the current through the orifice. The apparatus thus includes a chamber which is subdivided into two portions 18 and 19 by an apertured wall 21. The portion 19 receives the particle bearing jet stream and isolates the particles from the measuring aperture as illustrated by the arrows 44, FIG. 5. The particle free liquid in the portion 18 flows along with the stream by Venturi action as shown by arrows 46. This flow maintains and stabalizes the jet stream so that it maintains its integrity until it passes through the opening 22.

By providing a well-defined jet stream line which contains a monofile of particles, it is possible to employ optical energy sensors such as a laser, fibreoptic, photocell or microscope arrangement for analyzing the particles in the stream as it travels through the particle free liquid.

Figure 6:
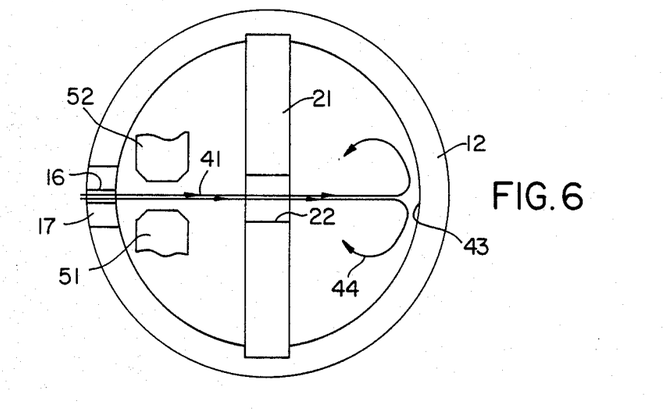
FIG. 6 is a view showing sensing of the particles in the jet stream line as the jet stream travels through the particle free fluid.
Figure 7:
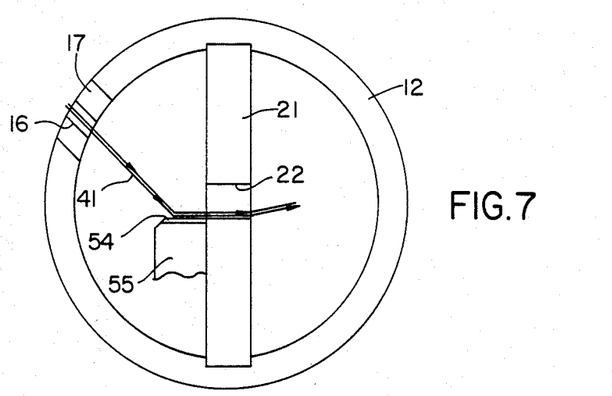
FIG. 7 is a view showing an offset orifice providing particles to a focal plane for microscopic or other optical viewing.
Figure 8:
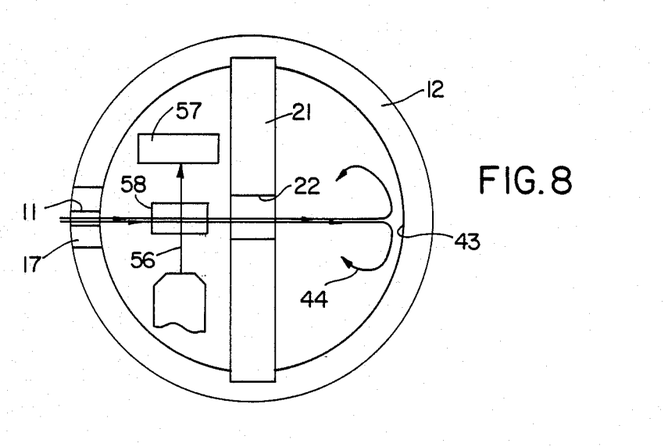
FIG. 8 is a view showing a laser beam and transducer for analyzing the particulate matter in the jet stream line.

FIG. 6 schematically shows an optical fiber bundle 51 supplying light on one side of the jet stream and an optical fiber bundle 52 on the other side to detect particles crossing the light beam. Alternatively, the elements 51 and 52 could be the condensor and objective lenses of a microscope for viewing the particles with suitable beams and by suitable means. FIG. 7 shows the jet stream 53 at an angle to the aperture or opening 22. The jet stream strikes a plate 54 where it is precisely located. This plate is a suitable object lens 55 of a microscope focused in front of the surface to analyze the impinging particulate matter. FIG. 8 schematically shows a laser beam 56 striking particles and one or more transducers 57 and 58 for receiving transmitted, reflected, scattered or fluorescent light of one or more appropriate wave lengths. It is apparent that any known means for analyzing particles flowing in a stream can be used to analyze the particles which travel as a monofile in the jet stream.

In the prior art and in the embodiment of FIGS. 1-8 the analyzing orifice is formed in the wall which interfaces with the particulate matter laden liquid. This means that particles are not always centered in the orifice since they may be drawn in from directly in front of the orifice or swing in from the side. The fluid dynamic and the sensory energy field in the orifice and around the orifice are not uniform. Thus, the size of the output electrical pulse can be affected by the position of the particle trajectory. In prior art apparatus this has been overcome by providing a laminar stream of fluid containing the particulate matter within one or more sheath of particle free fluid. However, the prior art systems are not closed systems in which the liquid flow of the suspension could be accurately measured without substantial structural complexity and cost.

Figure 9:
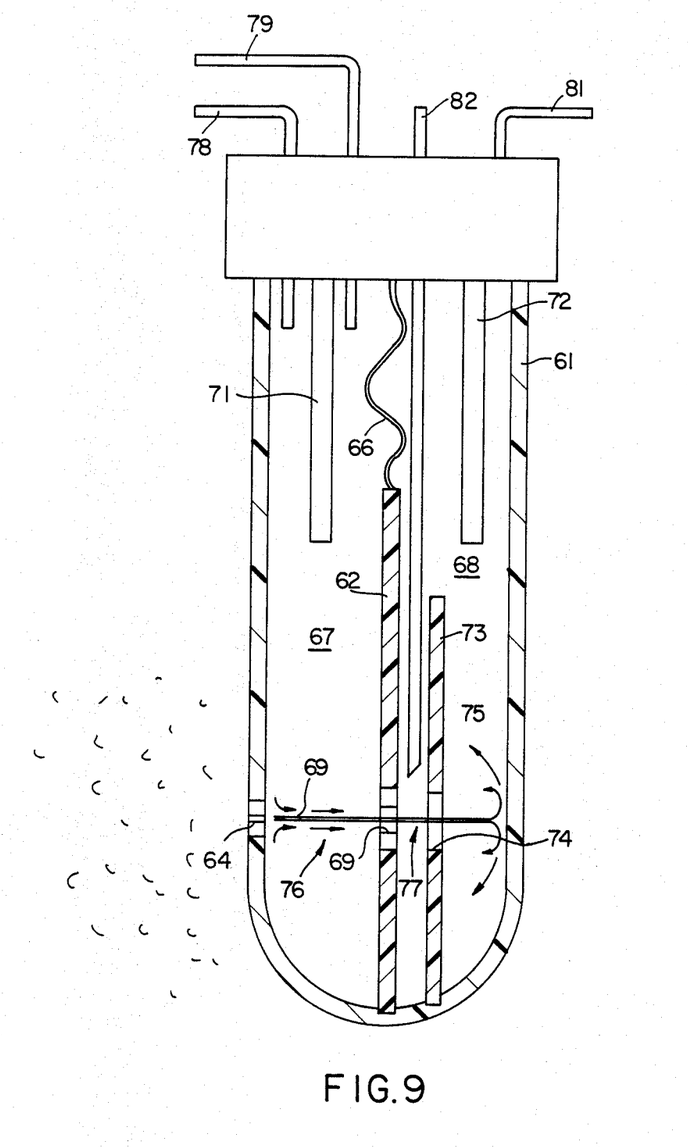
FIG. 9 is a sectional view of another embodiment of the invention. This also shows means for separating two portions of the chamber except at the sensing orifice.

FIG. 9 shows a closed system in which a jet stream of the type described in connection with the embodiment of FIG. 1 is formed by a first orifice and directed through a second analyzing orifice before it travels into the dirty portion of an associated chamber. In this way the particle carrying jet can be centered in the analyzing orifice by the jet stream formed at the first aperture and maintained by the Venturi flow.

Referring now to FIG. 9 the apparatus includes a vessel 61 which is divided into two chambers by a wall 62. The wall accommodates a jeweled analyzing orifice 63 disposed opposite and spaced from the input orifice 64 formed in the wall of the vessel 61. The wall 62 includes an insulating flexible diaphragm portion 66 which moves to maintain virtually equal pressure in the two chambers 67 and 68 defined by the wall 62 and diaphragm 66. Thus, as the liquid jet stream 69 is formed by the opening 64 and entrains particle free liquid in the chamber 67 the diaphragm moves to the left as seen in the figure to maintain the pressure and supply the necessary liquid to make up for that which has been entrained. In this embodiment the measuring electrodes 71 and 72 are placed in chambers 67 and 68 respectively to provide current through the counting and analyzing orifice 63. The particles which form a monofile in the jet stream are directed through the center of the measuring aperture where each of the particles is subjected to the same field. The chamber 68 includes a wall or barrier 73 which includes an opening or aperture 74 through which the jet flows to deposit particulate laden liquid in the portion 75 of the chamber 68. The particles in the jet stream may be optically analyzed as described above with reference to FIGS. 1-8 at the regions 76 or 77 or both. During priming of this compound transducer chamber clean liquid is introduced into the chamber 67 by a tube 78 and can be removed by a tube 79. Similarly, clean liquid is introduced into chamber 68 by tube 82 and outflow liquid is removed from the chamber 68 by tube 81 which may also function as the measuring tube.

Figure 10:
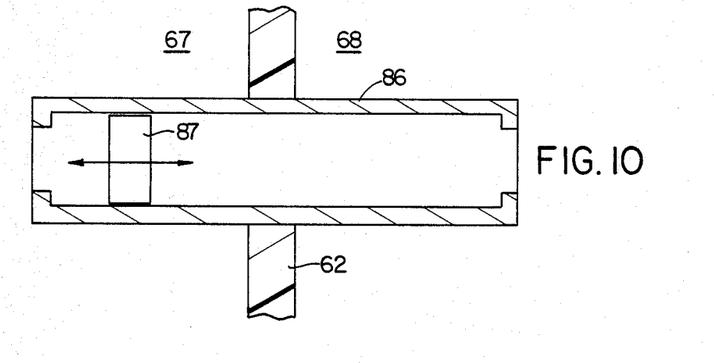
FIG. 10 is a partial view showing means for transferring fluid from the output side to the input side of a multi-chambered apparatus to make up liquid entrained by the fluid jet stream of the inflowing suspension.

FIG. 10 shows another means of providing compensating fluid. A piston assembly 86 made of insulating material communicates between chambers 67 and 68. The piston 87 moves to make up fluid.

Figure 11:
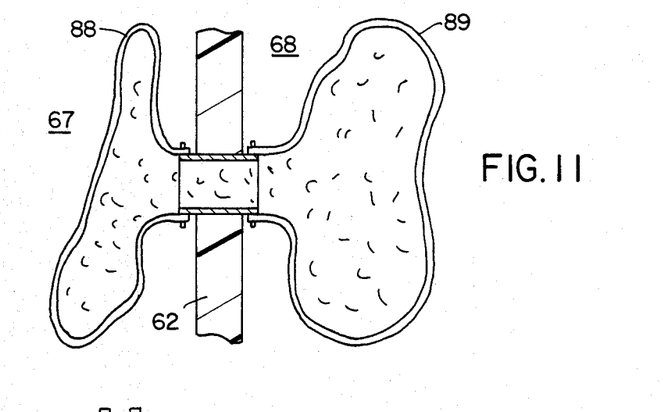
FIG. 11 is a partial view showing means for transferring fluid from the output chamber to the input chamber with a slight pressure to make up liquid entrained by the liquid jet stream and to form an enveloping sheath for sheath flow.
Figure 12:
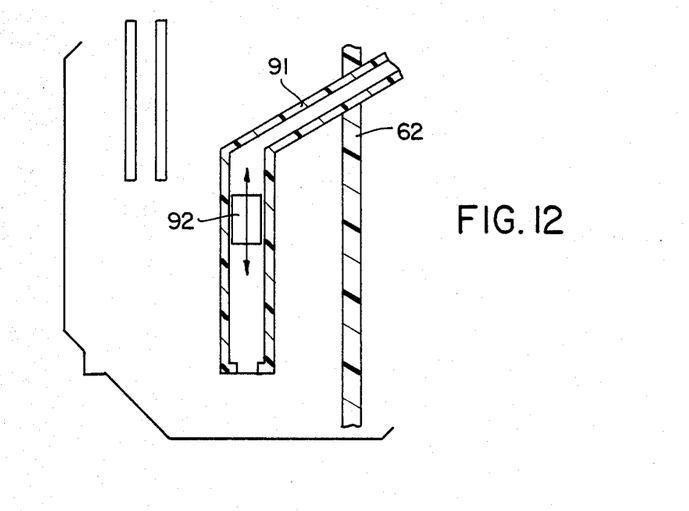
FIG. 12 is a partial view showing another means for transferring liquid from one chamber to the other with pressure for supplementing sheath flow.
Figure 13:
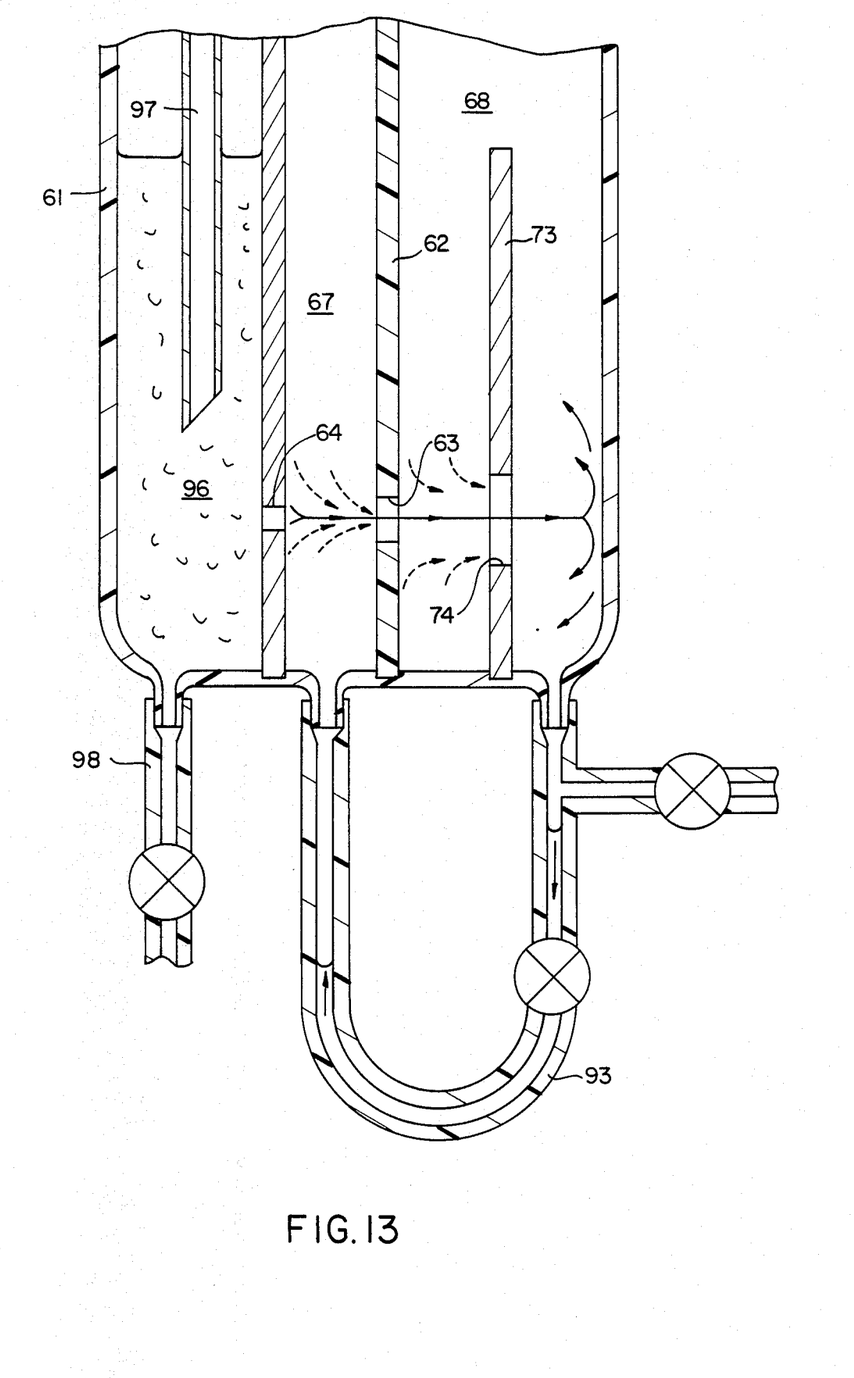
FIG. 13 is a partial view showing a U-tube for generating pressure and making up entrained liquid and for electrical isolation.

FIG. 11 shows a pair of liquid filled balloons 88 and 89 made of or filled with insulating material, one on each side of the wall. During operation the balloon 89 contracts and the balloon 88 expands. If the material of the balloon 89 is thick and resilient it can provide pressure to the fluid in chamber 67 causing sheath flow. FIG. 12 shows another means for providing make up liquid and pressure. The insulating assembly includes a tube 91 including a piston 92. In operation the piston is lifted to the top when a test run is commenced. The weight of the piston provides additional sheath forming pressure. FIG. 13 shows a U-tube 93 which is filled with a dense liquid that is immiscible with the liquid in the chambers 67 and 68. Pressure is equalized by movement of the fluid. The assembly includes a portion 96 which is filled with particle laden liquid by tube 97 and drained at tube 98. It is apparent that many other means can be used to provide the make up liquid either with or without pressure. The key is that the volume of fluid in the chambers remains constant so that the liquid flowing out of the tube 81 during a run is an exact measure of the volume of particle laden liquid which travels through the center of the counting and analyzing orifice 63.

Figure 14:
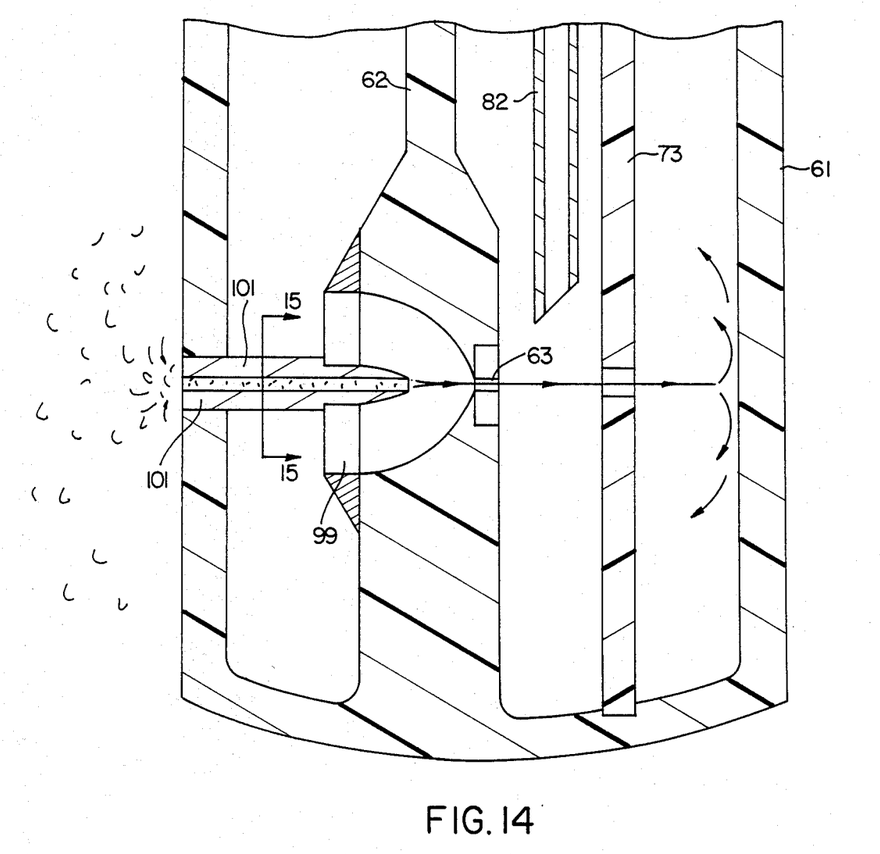
FIG. 14 is a view similar to that of FIG. 9 showing blades which create a spiralling action in the outer fluid stream to enhance focusing of the jet stream.
Figure 15:
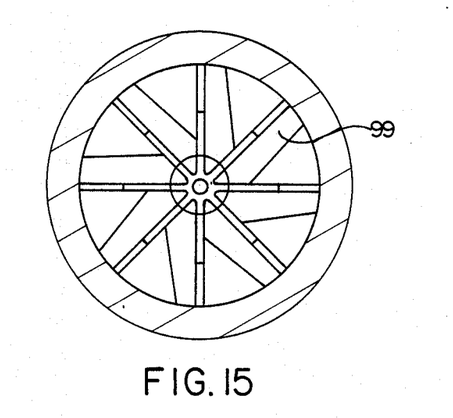
FIG. 15 is a view along the line 15—15 of FIG. 14 showing the blades.

As is known, stabilization of a very long focused jet stream is enhanced by introducing a spiral action to the fluid. For this purpose blades or vanes 99, FIGS. 14 and 15, may be disposed adjacent the aperture 63 to provide the desired action. The input orifice may be in the form of a tube 101.

In the embodiments described the pressure differential at the input orifice is described as being created by applying a vacuum to the closed chamber. It is apparent, however, that the particulate laden liquid can be under pressure to jet it into the chamber including particle free liquid.

Thus, there is provided an improved method and apparatus for generating stable fully-controlled stream lines of suspended particulates in such a way that they predictably traverse one or more critical sensing regions within a partially subdivided closed vessel. The invention teaches a method for making precisely this same volume of fluid traverse any given plane placed across the fully controlled trajectory of the inflowing suspension within the chamber, this exact equivalence being maintained throughout the counting period of the apparatus. This provides both high resolution analytic capability and high precision counting capability separately as well as in combination. The constant unidirectional fluid movement is achieved by shooting a jet of the suspension into the compound fluid-primed transducer chamber from a fine capillary or orifice at the inflow end of the chamber; allowing this jet to pass coherently through the contained particle free fluid to some distal portion of the chamber in which waste or analyzed suspension can accumulate safely for the duration of the counting cycle; permitting the pressure represented by this accumulating fluid is displace its own volume of particle free fluid from a portion of that distal chamber; and straddling the created stable stream lines with various sensors for interrogating, analyzing and counting the suspended particulate matter. Furthermore, the initially contained particle free fluid is used to satisfy the venturi needs of the jet stream in its transit through the chamber.

What is claimed:
1. The method for the analytic counting of particulates suspended in a liquid medium including the steps of passing the particulate-carrying fluid through an aperture into a first region of a chamber containing particulate-free fluid, passing the stream of particulate- carrying fluid so produced through one or more sensors for analytically counting the particulates, passing the particulate-carrying stream through an opening in a barrier straddling the jet stream into a second region of the chamber, said barrier serving to preserve the volume of the first region in which the particle-carrying stream line is maintained, said barrier preventing direct recirculation of previously sensed particles through the opening straddling the jet stream into the first region while maintaining within said chamber, spaced from the opening between the first and second regions, free, direct and unhindered fluidic communication between the first and second regions and passing a volume of particulate-carrying and/or particulate-free fluid through a single output port so that the volume entering the chamber, the volume leaving the chamber, and the volume of particulate-carrying fluid passed through the sensors are all exactly equal, no portion of the particulate-carrying fluid being permitted to return to the regions of the sensors.

2. In a particle analyzing apparatus including a vessel containing a suspension of particulates in a fluid, an aperture for entry of said particulate-carrying fluid into a chamber containing particulate-free fluid, one or more sensors for analytically counting said particulates, and a source of vacuum and/or pressure for causing flow of the particulate-carrying fluid into said chamber, the improvement consisting of the chamber being a closed chamber wherein the same amount of fluid leaves the chamber as enters the chamber, at least one barrier disposed in the chamber to form a region into which the sensed particulate-carrying fluid enters to prevent, for the duration of the counting period, recirculation of previously sensed or transferred particulate-carrying fluid to the regions of the chamber where it would interfere with the sensors and means within said chamber for maintaining free, direct and unhindered fluidic communication of fluid within the chamber.

3. An apparatus as in claim 2 in which the period of counting is determined by a measured volume of fluid entering or leaving the measuring chamber.

4. An apparatus as in claim 3 in which one of the sensors is an orifice through which current flows.

5. An apparatus as in claim 4 in which the entry aperture also serves as the sensing orifice.

6. An apparatus as in claim 5 in which the barrier is a thin piece of material with at least one aperture in it, located so that the stream of particulate-carrying fluid passes through the aperture.

7. An apparatus as in claim 4 in which the orifice is placed in the line of particulate-carrying fluid stream spaced from the input orifice.

8. An apparatus as in claim 7 in which the barrier is a thin piece of material with at least one hole in it, located so that the stream of particulate-carrying fluid emerging from the orifice passes through the particulate trapping hole.

9. An apparatus as in claim 3 in which at least one of the sensors is an optical sensor placed downstream from the input aperture.

10. An apparatus as in claim 7 in which the optical sensor measures the fluorescence of labelled or autofluoresence particulates.

11. An apparatus as in claim 9 in which the optical sensor measures light scattering of the particulates.

12. An apparatus as in claim 4 in which a single or compound second sensor is placed downstream from the input aperture and a portion of such sensor is optical in nature.

13. An analyzing apparatus of the type including a sample vessel for containing a particulate laden liquid, and a chamber including an analyzing orifice communicating with said vessel, said chamber adapted to contain a particle-free liquid and means dividing said chamber into a first clean portion and a second portion, said means including an opening whereby when differential pressure is applied between the particle laden liquid of said vessel and the particle free liquid of said chamber, particle laden liquid jets through said orifice through the particle free liquid of the first region of said chamber into the second portion, said dividing means spaced from the top of the vessel to provide direct, free and unhindered fluidic communication between said first and second portions.

* * * * *